US005529750A

United States Patent [19]
Kochte

[11] Patent Number: 5,529,750
[45] Date of Patent: Jun. 25, 1996

[54] CONTAINER WITH INTERNAL LIQUID DISTRIBUTION PORT FOR HOLDING EQUIPMENT WITH INTERNAL PASSAGES DURING STERILIZATION

[75] Inventor: Werner W. Kochte, Kent, Ohio

[73] Assignee: Steris Corporation, Mentor, Ohio

[21] Appl. No.: 302,583

[22] Filed: Sep. 8, 1994

[51] Int. Cl.⁶ .................................. A61L 2/00; A61L 9/00
[52] U.S. Cl. ...................... 422/28; 422/296; 422/297; 422/301; 422/302; 134/95.1; 134/99.1; 134/102.1
[58] Field of Search ........................ 422/295, 296, 422/297, 300, 301, 302, 905, 28; 134/95, 99, 102; 206/63.5, 459.5

[56] References Cited

U.S. PATENT DOCUMENTS

| | | | |
|---|---|---|---|
| 1,861,768 | 6/1932 | Wappler | 422/292 |
| 4,247,517 | 1/1981 | Sanderson et al. | 422/26 |
| 4,296,862 | 10/1981 | Armentrout et al. | 206/439 |
| 4,512,498 | 4/1985 | Leibinger | 220/371 |
| 4,617,178 | 10/1986 | Nichols | 422/310 |
| 4,661,326 | 4/1987 | Schainholz | 422/310 |
| 4,671,943 | 6/1987 | Wahlquist | 422/300 |
| 4,704,254 | 11/1987 | Nichols | 422/28 |
| 4,731,222 | 3/1988 | Kralovic et al. | 422/37 |
| 4,800,164 | 1/1989 | Bisconte | 435/300 |
| 4,959,199 | 9/1990 | Brewer | 422/300 |
| 5,084,251 | 1/1992 | Thomas | 422/300 |
| 5,091,343 | 2/1992 | Schneider et al. | 422/297 |
| 5,106,366 | 4/1992 | Steppe | 604/30 |
| 5,217,698 | 6/1993 | Siegel et al. | 422/295 |
| 5,238,660 | 8/1993 | Dietwart | 422/295 |
| 5,275,668 | 1/1994 | Dell et al. | 134/10 |
| 5,281,400 | 1/1994 | Berry, Jr. | 422/295 |
| 5,288,467 | 2/1994 | Biermaier | 422/116 |
| 5,305,876 | 4/1994 | Brigham | 206/63.5 |
| 5,310,524 | 5/1994 | Campbell et al. | 422/33 |
| 5,340,551 | 8/1994 | Berry, Jr. | 422/300 |
| 5,346,677 | 9/1994 | Risk | 422/297 |

FOREIGN PATENT DOCUMENTS

| | | |
|---|---|---|
| 3405268A1 | 9/1985 | Germany . |
| 2165754 | 4/1986 | United Kingdom . |

OTHER PUBLICATIONS

"Sterile Processing . . . Just in Time", Steris Advertising Brochure Steris System 1, ©1992.

Primary Examiner—Robert J. Warden
Assistant Examiner—N. Bhat
Attorney, Agent, or Firm—Fay, Sharpe, Beall, Fagan, Minnich & McKee

[57] ABSTRACT

A microbial decontamination system includes a lower housing portion (10) which receives a removable tray (12). The tray (12) defines a cassette receiving basin, a pair of anti-microbial fluid outlets (28, 64) and a drain (50). A pump (54) and associated plumbing circulates the anti-microbial fluid from the drain through the pair of outlets. A cassette (B) has a lower portion (FIGS. 8–10) which is configured to match the tray's basin and an upper portion (FIGS. 5–7) which is received on the lower cassette portion in an airborne microbe blocking relationship. The cassette bottom portion has an inlet (32) which receives the anti-microbial fluid and a baffle plate (44) adjacent the inlet having a plurality of apertures (96) for distributing the anti-microbial fluid within the cassette. The cassette defines a second inlet (66) which is interconnected with the tray second outlet also for receiving the anti-microbial fluid. The second inlet receives a removable distribution port assembly (68). The distribution port assembly has a plurality of nipples (116) for interconnection with hoses (118) that are connected with internal passages of items to be microbially decontaminated. A variety of distribution ports are provided, with different numbers of nipples, to provide an appropriate number of connections for the items to be microbially decontaminated.

15 Claims, 6 Drawing Sheets

CONTAINER WITH INTERNAL LIQUID DISTRIBUTION PORT FOR HOLDING EQUIPMENT WITH INTERNAL PASSAGES DURING STERILIZATION

BACKGROUND OF THE INVENTION

The present invention pertains to the art of microbial decontamination. It finds particular application in conjunction with sterilizing medical equipment with liquid sterilants and will be described with particular reference thereto. It will be appreciated, however, that the invention is also applicable to disinfecting systems as well as to microbial decontamination systems using fluid, e.g., gas or liquid, anti-microbial agents for sterilizing, disinfecting, or decontaminating a wide range of items, including dental instruments, endoscopes, laboratory equipment, manufacturing equipment, and other equipment and items on which it is desirable to eliminate microbial life forms.

Sterilization connotes the absence of all life forms, including bacterial endospores which are the living organisms most resistant to conventional sterilants. Disinfection, by distinction, only connotes the absence of pathogenic life forms. Microbial decontamination is generic to both sterilization and disinfection.

Medical equipment is often sterilized at high temperatures. Commonly, the equipment is sterilized in a steam autoclave under a combination of high temperature and pressure. Endoscopes, rubber and plastic devices or portions of devices, such as lenses, and the like may be destroyed or have their useful lives severely curtailed by this heat and pressure.

More sensitive medical equipment is often sterilized with ethylene oxide, which is thermally less severe than steam. The items must be exposed to the ethylene oxide for a relatively long duration, on the order of three and a half hours. Thereafter, eight to twelve hours are normally required for de-gassing or desorbing the ethylene oxide from plastic and other materials which are capable of absorbing the ethylene oxide. The pressurization and depressurization cycles of ethylene oxide sterilization may damage lens systems and other delicate instruments. Moreover, the ethylene oxide is relatively expensive. It is sufficiently toxic and volatile that extensive precautions are commonly taken to assure operator safety.

Liquid systems are used for sterilizing and disinfecting a wide variety of instruments, including instruments which are too heat sensitive or delicate for heat sterilization. A suitable liquid sterilization system is illustrated in prior U.S. Pat. No. 5,091,343 of the assignee herein. In the system of the earlier patent, items to be sterilized are inserted or placed in the tray of a cassette. A cover is placed on the cassette and the cassette is placed in a liquid sterilization unit. Within the unit, the cassette is filled with liquid sterilant, rinsed with a sterile rinse, and the rinse water drained. As the rinse water drained, sterile air is introduced to refill the cassette. Thereafter, the cassette is removed with its lid still in place such that the sterilized instruments are maintained in a sterile environment until the cassette is opened. Although this prior system has been successful, one of the drawbacks has been in assuring a flow of liquid sterilants through interior passages of medical instruments. The low pressure circulation of the liquid sterilant in the cassette did not assure sterilization of internal passages.

In accordance with the present invention, a new and improved anti-microbial apparatus and cassette therefor are provided which overcomes the above-referenced problems and others.

SUMMARY OF THE INVENTION

In accordance with one aspect of the present invention, a cassette for an anti-microbial system is provided. The cassette includes a lower tray or shell portion which receives and holds items to be microbially decontaminated. A cover or uppermost cassette portion closes the cassette in an airborne blocking microbe relationship. At least one passage into the cassette for receiving and discharging fluids such as liquid or gaseous anti-microbial agents and air, is provided. The passage is sufficiently tortuous that the entrance of airborne microbes is inhibited. A fluid distribution port is mounted to the lower cassette portion for connection with a source of anti-microbial fluid under pressure. Hoses are selectively connectable between the fluid distribution port and openings into internal passages of the items to be microbially decontaminated.

In accordance with a more limited aspect of the present invention, a check valve is provided in conjunction with the fluid port for permitting the introduction of fluid under pressure, but blocking a flow of airborne microbes.

In accordance with another more limited aspect of the present invention, the anti-microbial system includes a tray having a well or basin for receiving the cassette. The basin is connected with a source of anti-microbial fluid and has a port for interconnection with the fluid distribution port for providing fluid sterilant under pressure thereto.

One advantage of the present invention is that it facilitates effective microbial decontamination of medical and other items with fluid sterilants and disinfectants.

Another advantage of the present invention is that it improves sterilization/disinfection assurance of instruments with internal passages.

Another advantage of the present invention is that it maintains a microbe-free condition of the items during temporary or longer term storage.

Yet another advantage of the present invention is that it facilitates maintaining an organized inventory of microbially decontaminated items.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
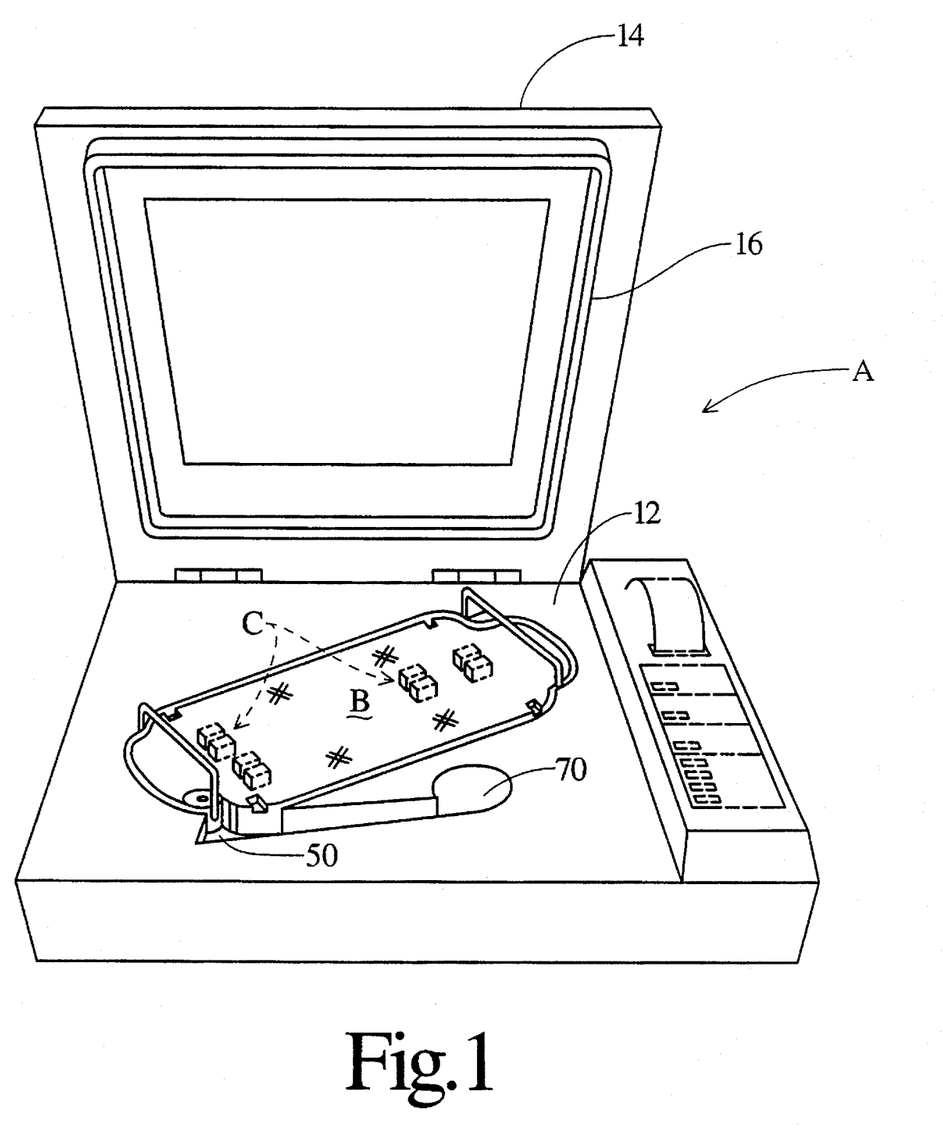
FIG. 1 is a perspective view of a microbial decontamination system in accordance with the present invention.

With reference to FIG. 1, a microbial disinfecting apparatus A includes a base portion 10 upon which a tray 12 is removably mounted. The tray defines a basin for removably receiving one of a plurality of instrument receiving cassettes B. Each cassette may be configured or fitted with appropriate mounting structures C for holding or arranging medical instruments or other items. After the cassette is placed in the basin, a lid 14 is closed causing a gasket 16 to seal the basin and cassette from the ambient atmosphere. The microbial decontaminating apparatus in a carefully controlled cycle floods the basin filling the cassette and surrounding the medical instruments, cassette, or other items to be microbially decontaminated with a fluid anti-microbial agent, such a liquid solution or a gas. The anti-microbial fluid is drained and a microbe-free rinse fills the basin and cassette to flush or remove any chemical residue. After the rinse has been drained, the lid is opened and the cassette is removed as a unit containing microbially decontaminated items. The cassette is configured such that it permits the ingress and egress of the fluid anti-microbial agent and rinse solutions but prevents microbial contamination in the ambient air from reaching the enclosed medical instruments or other items. The cassette with the contained microbially decontaminated items may be inventoried and stored until the microbially decontaminated items are needed.

Figure 2:
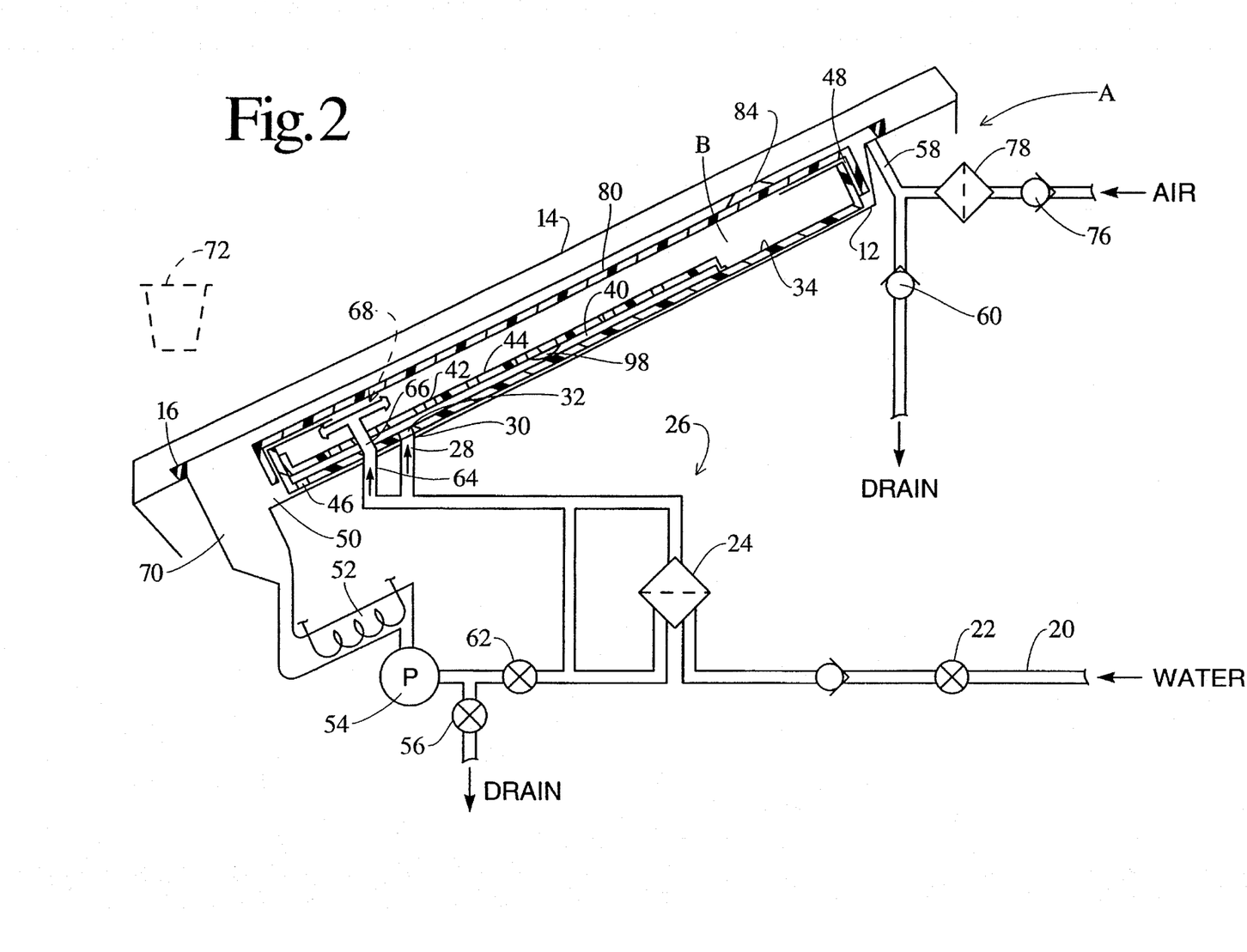
FIG. 2 is a diagrammatic illustration of the fluid flow paths for the system of FIG. 1.
Figure 3:
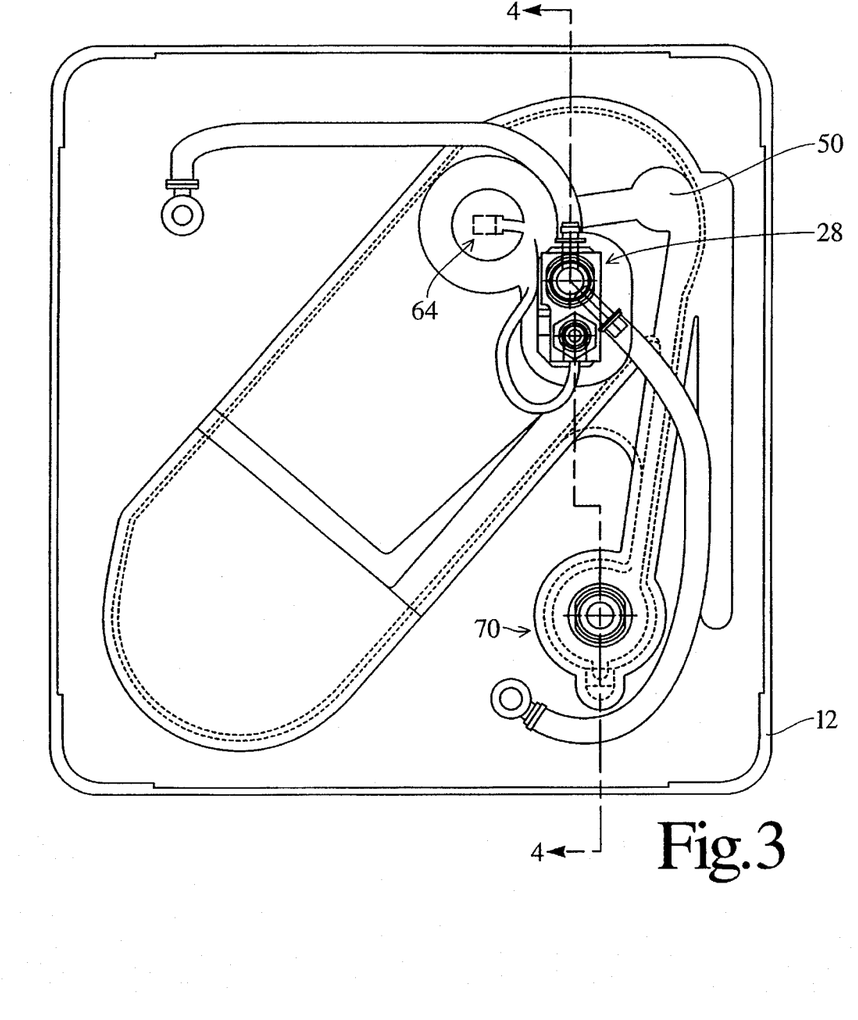
FIG. 3 is a bottom view of a cassette receiving tray of the system of FIGS. 1 and 2.
Figure 4:
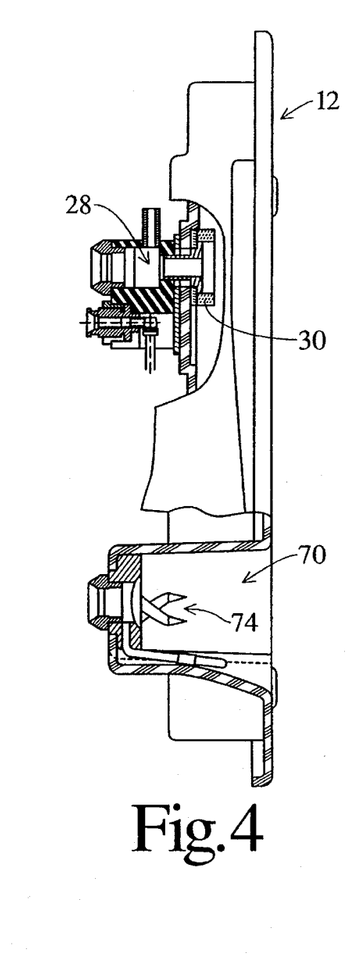
FIG. 4 is a side view in partial section of the tray of FIG. 3.

With reference to FIGS. 2, 3, and 4, in a liquid embodiment, tap water is received at an inlet 20. A valve 22 selectively enables the water to flow to a microbial decontaminating means 24 for microbial decontaminating the received water. In the preferred embodiment, the microbial decontaminating means is a filter which mechanically separates microbes and other contaminants from the received water. Strong ultra-violet light radiation, chemicals, and the like are also contemplated. When the valve 22 is opened, incoming water flows through the filter 24 becoming microbially decontaminated and flows through a tubing system 26 to a first fluid supply outlet 28. A seal 30 around the first fluid supply outlet 28 directs water into a first fluid receiving inlet 32 in a lower wall 34 of the cassette B.

The fluid flows through a tortuous path 40 defined between the bottom wall 34 and apertures 42 in a baffle plate 44 of the cassette. The fluid flows into the interior of the cassette immersing the items to be microbially decontaminated. Fluid flows out of the cassette through a cassette drain outlet 46 and vent passage 48 and the tubing system 26 conveys the fluid from a basin drain 50 to a heater 52 and a pump 54. A drain valve 56 selectively enables the fluid to be drained from the system. As additional microbe-free water flows into the system, air is displaced through a vent passage or vent outlet 58 which is connected by a check valve 60 with the drain.

A recirculating valve 62 allows the pump to pump the fluid through the tubing system back to the fluid outlet 28 and to a second fluid supply outlet 64 in the tray and a second fluid inlet 66 in the cassette. A fluid distribution port assembly 68 is mounted in the second inlet.

The received liquid also fills a well 70 which defines a reagent receiving chamber for receiving anti-microbial agents, wetting agents, detergents, and other treatment chemicals for improving the cleaning and microbial decontaminating effect. An ampule 72 contains peracetic acid or other strong oxidant compositions or reagents which react to form strong oxidants, as well as buffers and corrosion inhibitors to be introduced into the well a cutting assembly 74 opens the cup releasing its ingredients. After the system is filled with water, inlet valve 22 is closed. The recirculating valve 62 is opened and the pump 54 is actuated. As fluid is drawn through the well by the pump, the reagents mix with the water forming a microbial decontaminating or other anti-microbial solution. The microbial decontaminating solution is circulated through the tubing system 26 back to the fluid distribution port assembly 68 and to the inlet 32 through the tortuous path 40 and distributed among the many inlets of the baffle plate 44. As the pump 54 circulates the sterilant solution, some of the sterilant flows through the microbial decontaminating filter 24 microbial decontaminating it. Other solution flows through the vent 58 and other tubing and fluid contacting surfaces.

After the anti-microbial fluid has been circulated from the pressure port 66 through the interior of items to be microbially decontaminated and maintained in contact with the items in the cassette and all tubing valve and other surfaces between the microbial decontaminating means 24 and the cassette for a selected duration, the recirculation valve 62 is closed and the drain valve 56 is opened. The anti-microbial fluid is pumped or drained from the system. In this manner, all the tubing and valve surfaces with which the rinse fluid comes in contact are sterilized or microbially decontaminated by the anti-microbial fluid.

To flush any chemical residue, the fill valve 20 is again opened so that tap water flows through filter 24 through the microbially decontaminated tubing system 26 to the fluid outlet 28. The microbially decontaminated rinse solution continues to flow into the basin 10 until all the air is displaced. Pump 54 may be actuated again to recirculate the rinse solution to the distribution port 66 through internal passages of the items and through inlet 32 over the surfaces of the items for a preselected duration. Thereafter, the drain valve 56 is opened and the rinse solution is drained. Air flows through a check valve 76 and the microbial decontaminating filter 78 such that sterile air fills the basin and cassette as the rinse and anti-microbial fluids are drained.

Alternately, other fluid anti-microbial agents can be utilized. Liquid glutaraldehyde and other liquid anti-microbial agents can be circulated analogously. Gaseous anti-microbial agents, such as ethylene oxide can be introduced at valve 22 and recirculated. The pump 54 pumps the gas back into a reservoir or tank at the end of a cycle.

Figures 5, 7:
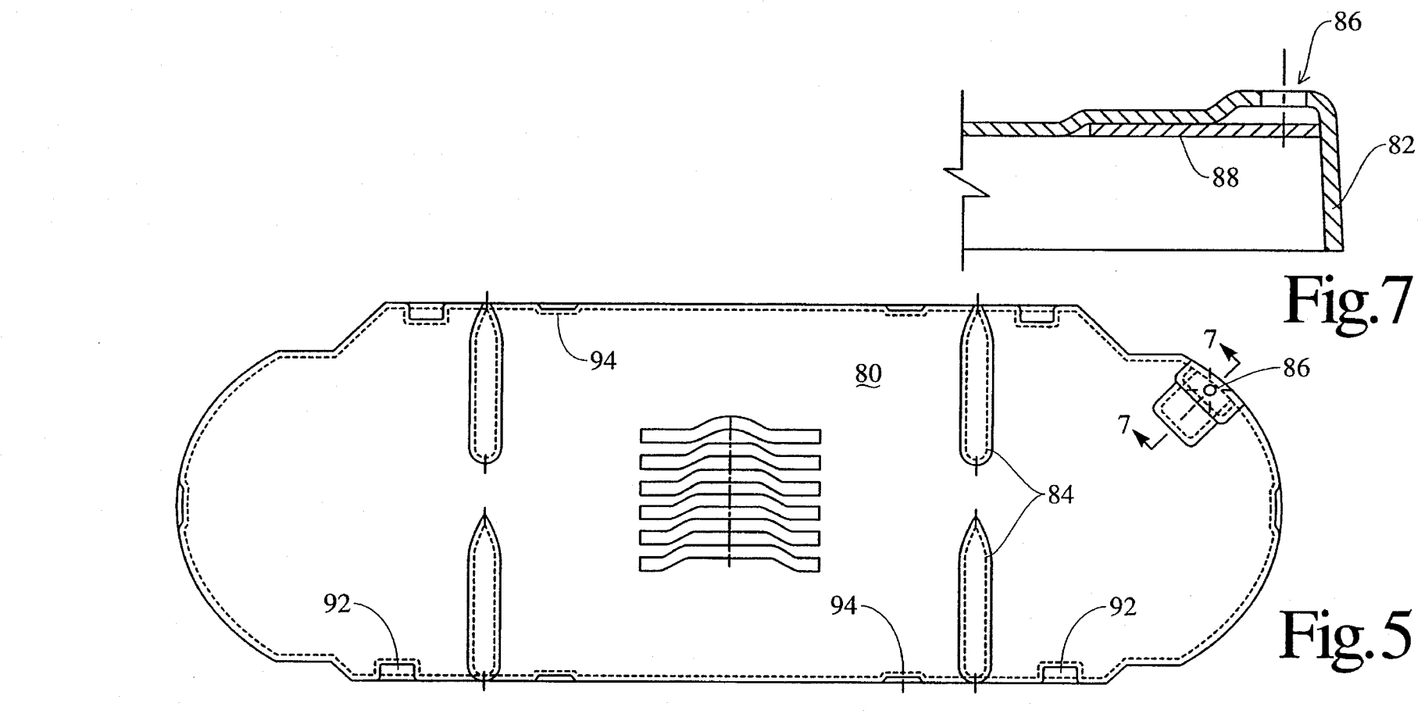
FIG. 5 is a top view of the top cassette portion.
FIG. 7 is a sectional view through section 7—7 of FIG. 5 illustrating a cassette vent portion.
Figure 6:
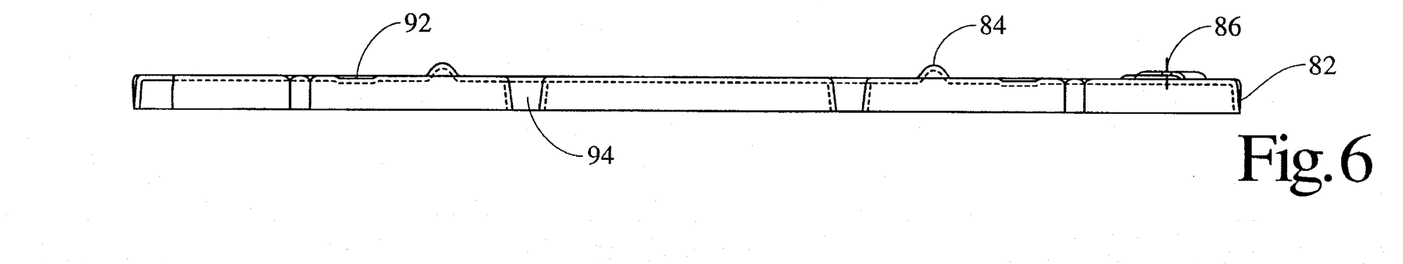
FIG. 6 is a side view of the cassette top portion.

With reference to FIGS. 5 and 6, the cassette B has a generally flat cover or upper portion 80 with a downward depending peripheral wall 82 extending peripherally therearound. Spacers 84 extend upward from the cassette cover to engage the sterilizer lid 14 such that lid urges the cassette into firm engagement with the seal 30. The spacers are configured such that no air is trapped by the spacers or the interaction between the spacers and the lid. Rather, all surfaces around the spacers become immersed in the anti-microbial fluid and are microbially decontaminated.

With reference to FIG. 7, the cover 80 includes an air inlet aperture 86 which has a resilient flap valve 88 therebelow. The flap valve pulls downward towards the interior of the cassette as fluid is drained, attempting to draw a vacuum therein. The flap permits air which is passed through the sterilizing air filter 78 to enter the cassette. However, once the cassette is removed from the tray and placed in the ambient atmosphere, the flap valve 88 prevents contaminating microbes from entering the cassette.

Figures 8, 10:
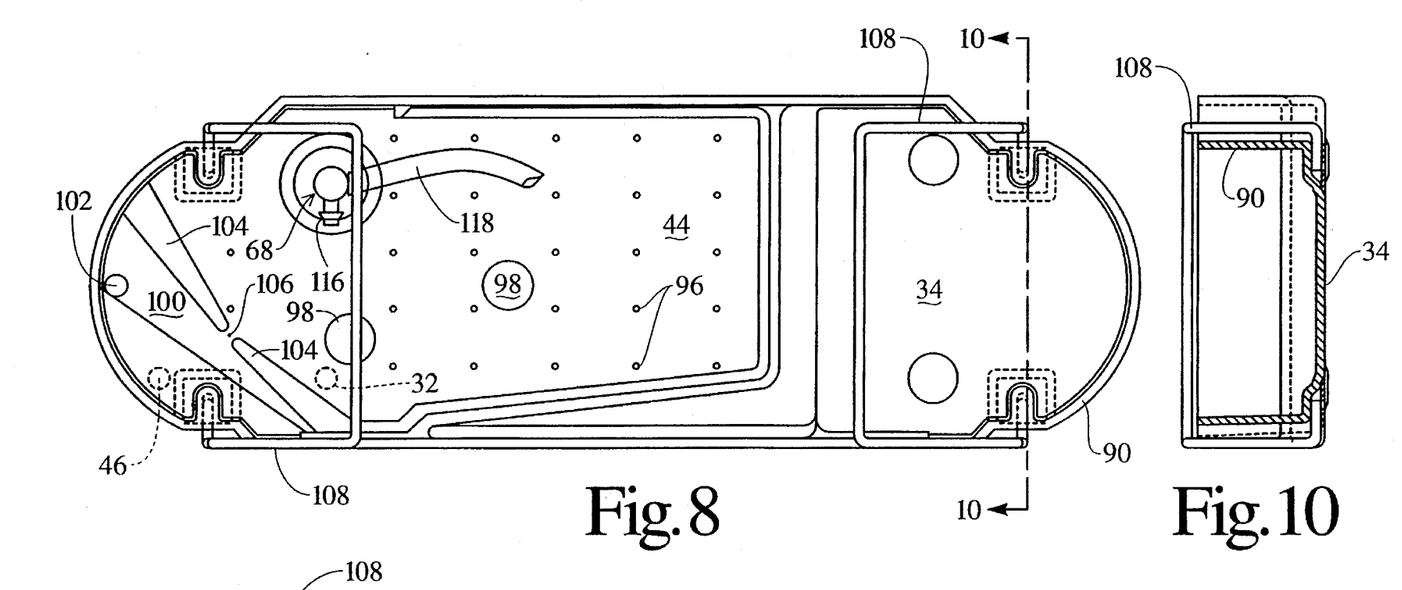
FIG. 8 is a top view of the lower portion of the cassette which is received in the reservoir of the tray.
FIG. 10 is an enlarged sectional view along section 10—10 of FIG. 8.
Figure 9:
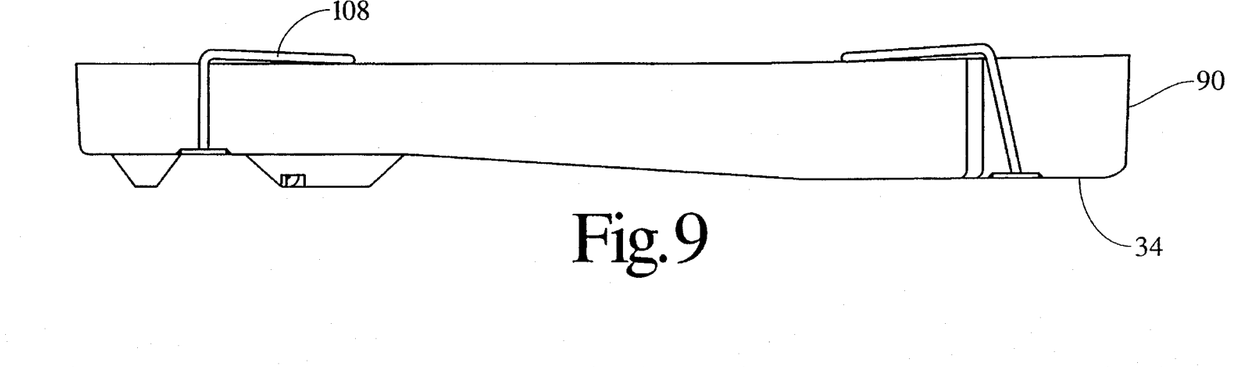
FIG. 9 is a side view of the tray of FIG. 8.
Figure 11:
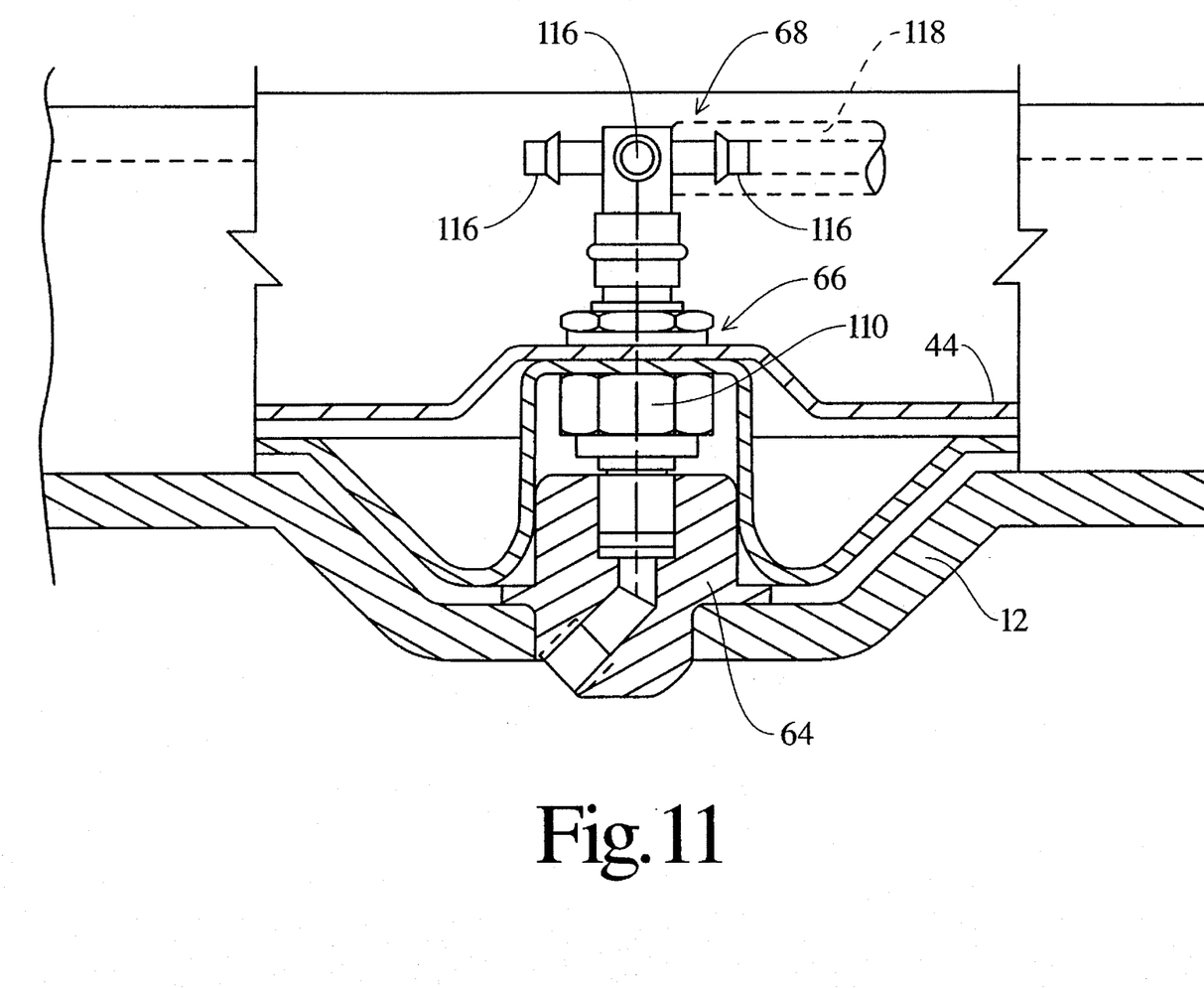
FIG. 11 is a sectional view of the lower cassette portion and interconnected portions of the tray adjacent the second fluid inlet.

With reference to FIGS. 8, 9, and 10, the cassette bottom wall 34 is surrounded by a peripheral wall 90 to define a cassette lower portion. Projections 92 and 94 in the cassette top portion engage the top and sides of the lower cassette portion peripheral wall 90 to define a vent and fluid passage therebetween. The passage defined between the top and the side walls is sufficiently tortuous that airborne microbes are prevented from entering the cassette interior.

The baffle plate 44 has a plurality of apertures 96 distributed therearound. The apertures are disposed offset from the inlet aperture 32. In this manner, the tortuous path 40 which is defined between the inlet aperture 32 and the baffle plate nozzle apertures is sufficiently tortuous that air borne microbes are inhibited from entering the cassette. The baffle plate includes a projection 98 which projects downward toward the cassette bottom wall to maintain the baffle plate and the cassette in the spaced relationship. The baffle plate also defines a canted surface section 100 adjacent the drain outlet 46. The canted surface portion extends over the drain outlet and has an aperture 102 offset from the drain outlet 46. Liquid then flows to the edge of the canted portion onto the lower surface 34 and down to the drain aperture 46. In this manner, a tortuous path is again defined between the drain aperture and the interior of the cassette. Downward projections 104 provide a barrier between the inlet 28 and outlet 46 so that the liquid pumped into the inlet flows through the baffle plate nozzle apertures 96 primarily rather than directly to the outlet. A small vent passage 106 is defined through the barrier 104 to assure that no ambient air is trapped and to drain the baffle interspace during draining cycles. When the pump 54 is activated, some liquid will, of course, flow through this barrier vent but the majority will be discharged through the baffle plate apertures 96.

A pair of handles 108 are interconnected with the cassette lower portion to facilitate lifting of the cassette without accidental removal of the cassette cover.

With continuing reference to FIG. 8 and further reference to FIG. 11, the second fluid inlet 66 includes a first fitting 110 which has an internal check valve. The fitting 110 is received in the second fluid supply outlet 64 of the tray to define a fluid tight seal. The fitting 110 receives circulated anti-microbial fluid under pressure, sufficient pressure to open the check valve. The bottom wall 34 of the cassette lower wall defines a well 112 within which the check valve fitting 110 is received. The distribution port assembly 68 has a lower or inlet end that is frictionally received in an upper end of the check valve fitting 110 and held in place by a quick release fitting 114. The distribution port assembly 68 includes at least one nipple 116 that frictionally receives a tube 118 for connection to an internal passage of one of the items being microbially decontaminated. Preferably, a plurality of distribution port assemblies 68 are provided with a variety of different numbers of nipples, e.g., with 1–6 outlet nipples 116. The number of nipples on the distribution port 68 is selected to correspond to the number of internal passage connections which are to made with the items to be microbially decontaminated. Alternately, caps may be provided for the nipples to which no hose connection is made. In operation, the anti-microbial fluid is circulated from the second tray outlet 28 through the check valve fitting 110, and the distribution port assembly 68. The fluid flow is divided among the nipples and conveyed by the tubing 118 to and through the internal passages of the item.

The invention has been described with reference to the preferred embodiment. Obviously, modifications and alterations will occur to others upon reading and understanding the preceding detailed description. For example, the bottom wall and the baffle plate may be designed with appropriate ridges, partitions, depressions, and the like such that the cassette is dedicated to accommodating a preselected type of medical apparatus, items, or other equipment. Larger and smaller cassettes may also be provided. A plurality of smaller cassettes might even be provided within the basin and have their contents sterilized concurrently. It is intended that the invention be construed as including all such modifications and alterations insofar as they come within the scope of the appended claims or the equivalents thereof.

Having thus described the preferred embodiment, the invention is now claimed to be:

1. In a method of microbial decontamination including placing an article which has an internal passage in a cassette lower portion, placing a cassette top portion matingly on the cassette lower portion in an airborne microbe blocking relationship, feeding an anti-microbial fluid into the cassette through a first inlet until the article is completely immersed in the anti-microbial fluid, and draining the anti-microbial fluid from the cassette, the improvement comprising:

connecting a distribution port assembly into a second inlet in the cassette lower portion, which distribution port assembly has an interior passage that receives the anti-microbial fluid from the second inlet and has at least one fitting through which the anti-microbial fluid is discharged;

connecting a tubing length between the fitting and the internal passage of the article;

feeding the anti-microbial fluid under pressure (i) through the second inlet such that the anti-microbial fluid passes through the distribution port assembly, through the tubing length, and through the internal passage of the article.

2. In a microbial decontamination system which includes a base portion, a tray mounted on the base portion, the tray defining: (i) a cassette receiving basin, (ii) a vent aperture adjacent an uppermost end, (iii) a drain adjacent a lowermost portion of the basin, (iv) a first fluid supply outlet for supplying an anti-microbial fluid and, (v) a second fluid supply outlet for supplying the anti-microbial fluid, a lid for selectively sealing the tray when in a closed position and providing ready access to the tray in an open position, a fluid anti-microbial supply disposed in the base portion for supplying anti-microbial fluid to the first and second outlets of the tray, and, a cassette removably disposed in the basin of the tray for holding items for microbial decontamination, the cassette including: a lower cassette portion configured in conformity with the tray basin, a first fluid inlet connected with the tray first fluid supply outlet for receiving the anti-microbial fluid to fill the cassette, a baffle disposed adjacent the first fluid inlet for providing a tortuous path between the first fluid inlet and items held in the cassette for microbial decontamination, the baffle rendering a path between the first inlet and the items sufficiently tortuous that airborne microbes are inhibited from recontaminating decontaminated items after the cassette is removed from the basin and a cassette top portion matingly received on the cassette lower portion in an airborne microbe blocking relationship, THE IMPROVEMENT COMPRISING the cassette having:

a second inlet for fluid interconnection with the tray second fluid supply outlet; and a distribution port connected with the second inlet and having at least one fitting for interconnection with an interior passage of an item held in the cassette for microbial decontamination.

3. In the microbial decontamination system as set forth in claim 2, the improvement further comprising:

the cassette second inlet having a check valve which is biased to a closed position to prevent an ingress of microbial contaminants and which check valve is selectively opened under pressure of the supplied anti-microbial fluids such that the anti-microbial fluids are passed through the fluid distribution port, and the internal passage of the item to be microbially decontaminated.

4. In the microbial decontamination system as set forth in claim 2, the improvement comprising:

the tray being removably mounted on the base portion and being replaceable with trays with different basin configurations.

5. In the microbial decontamination system as set forth in claim 4, the improvement comprising the tray including:

a fitting for receiving the anti-microbial fluid under pressure;

distribution passages for distributing the received anti-microbial fluid to the first and second fluid outlets.

6. In the microbial decontamination system as set forth in claim 2, wherein the anti-microbial fluid is a liquid anti-microbial solution, the improvement further comprising:

a means for circulating a microbially decontaminated rinse liquid to the first and second cassette inlets after the anti-microbial solution has been drained.

7. A microbial decontamination system comprising:

a base portion;

a tray mounted on the base portion, the tray defining: (i) a cassette receiving basin, (ii) a vent aperture adjacent an uppermost end, (iii) a drain adjacent a lowermost portion of the basin, (iv) a first fluid supply outlet for supplying an anti-microbial fluid and, (v) a second fluid supply outlet for supplying the anti-microbial fluid;

a lid for selectively sealing the tray when in a closed position and providing ready access to the tray in an open position;

a fluid anti-microbial supply disposed in the base portion for supplying anti-microbial fluid to the first and second outlets of the tray: and, a cassette removably disposed in the basin of the tray for holding a plurality of items for microbial decontamination, at least some of the items having internal passages, the cassette including:

a lower cassette portion configured in conformity with the tray basin;

a first fluid inlet connected with the tray first fluid supply outlet for receiving the anti-microbial fluid to fill the cassette;

a baffle disposed adjacent the first fluid inlet for providing a tortuous path between the first fluid inlet and items held in the cassette for microbial decontamination, the baffle rendering a path between the first inlet and the items sufficiently tortuous that airborne microbes are inhibited from recontaminating decontaminated items after the cassette is removed from the basin;

a second inlet for fluid interconnection with the tray second fluid supply outlet;

a plurality of interchangeable fluid distribution ports, each selectively interconnectable with the second inlet and each having different numbers of nipples;

a plurality of flexible tubes for interconnecting the nipples of the distribution port connected to the second inlet with the interior passages of the items held in the cassette for microbial decontamination;

a cassette top portion matingly received on the cassette lower portion in an airborne microbe blocking relationship.

8. A cassette for use in a microbial decontamination system which includes: a base portion; a tray mounted on the base portion, the tray defining: (i) a cassette receiving basin, (ii) a vent aperture adjacent an uppermost end, (iii) a drain adjacent a lowermost portion of the basin, (iv) a first fluid outlet for supplying an anti-microbial fluid and, (v) a second fluid outlet for supplying the anti-microbial fluid; a lid for selectively sealing the tray when in a closed position and providing ready access to the tray in an open position; a fluid anti-microbial supply disposed in the base portion for supplying the anti-microbial fluid to the first and second outlets of the tray, the cassette comprising:

a lower cassette portion configured in conformity with the tray basin;

a first fluid inlet connected with the tray first fluid outlet for receiving the anti-microbial fluid and filling the cassette;

a baffle disposed adjacent the first fluid inlet for providing a tortuous path between the first fluid inlet and items held in the cassette for microbial decontamination, the baffle rendering a path between the first inlet and the items sufficiently tortuous that airborne microbes are inhibited from recontaminating decontaminated items after the cassette is removed from the basin;

a second inlet for fluid interconnection with the tray second fluid supply outlet;

a distribution port removably connected with the second inlet and having at least one fitting for interconnection with an interior passage of an item held in the cassette for microbial decontamination;

a cassette top portion matingly receivable on the cassette lower portion in an airborne microbe blocking relationship.

9. The cassette as set forth in claim 8 wherein the second inlet further includes a check valve which is biased to a closed position to prevent an ingress of microbial contaminants and which check valve is selectively opened under pressure of the anti-microbial fluids.

10. A cassette for use in a microbial decontamination system which includes: a base portion; a tray mounted on the base portion, the tray defining: (i) a cassette receiving basin, (ii) a vent adjacent an uppermost end, (iii) a drain adjacent a lowermost portion of the basin, (iv) a first fluid outlet for supplying an anti-microbial fluid and, (v) a second fluid outlet for supplying the anti-microbial fluid; a lid for selectively sealing the tray when in a closed position and providing ready access to the tray in an open position; a fluid anti-microbial supply disposed in the base portion for supplying the anti-microbial fluid to the first and second outlets of the tray, the cassette comprising:

a lower cassette portion configured in conformity with the tray basin;

a first fluid inlet connected with the tray first fluid outlet for receiving the anti-microbial fluid and filling the cassette;

a baffle disposed adjacent the first fluid inlet for providing a tortuous path between the first fluid inlet and items held in the cassette for microbial decontamination, the baffle rendering a path between the first inlet and the items sufficiently tortuous that airborne microbes are inhibited from recontaminating decontaminated items after the cassette is removed from the basin;

a second inlet for fluid interconnection with the tray second fluid supply outlet;

a plurality of interchangeable fluid distribution ports, with different numbers of nipples, each distribution port being removably connectable with the second inlet;

a plurality of tubing lengths for connecting the nipples of the distribution port connected with the second inlet with interior passages of the items held in the cassette for microbial decontamination;

a cassette top portion matingly receivable on the cassette lower portion in an airborne microbe blocking relationship.

11. In a cassette for use in a microbial decontamination system which includes: a tray defining: (i) a cassette receiving basin, (ii) a vent adjacent an uppermost end, (iii) a drain adjacent a lowermost portion of the basin, (iv) at least one fluid outlet for supplying an anti-microbial fluid; a lid for selectively sealing the tray when in a closed position and providing ready access to the tray in an open position; a fluid anti-microbial supply disposed in the base portion for supplying the anti-microbial fluid to the outlet of the tray, the cassette including: a lower cassette portion configured in conformity with the tray basin, a first fluid inlet connected with the tray fluid outlet for receiving the anti-microbial fluid and filling the cassette, a baffle disposed adjacent the first fluid inlet for providing a tortuous path between the first fluid inlet and items held in the cassette for microbial decontamination, the baffle rendering a path between the first inlet and the items sufficiently tortuous that airborne microbes are inhibited from recontaminating decontaminated items after the cassette is removed from the basin, a cassette top portion matingly receivable on the cassette lower portion in an airborne microbe blocking relationship, the improvement comprising:

a second inlet for fluid interconnection with the tray fluid outlet;

a distribution port having a plurality of nipples removably connected with the second inlet;

tubing lengths for selectively interconnecting the nipples with internal passages of at least one of the items held in the cassette for microbial decontamination.

12. A cassette for receiving articles to be microbially decontaminated, the cassette comprising:

a lower cassette portion;

a first fluid inlet for receiving an anti-microbial fluid to fill the cassette;

a baffle disposed adjacent the first fluid inlet for providing a tortuous path between the first fluid inlet and articles received in the cassette for microbial decontamination, the baffle rendering a path between the first inlet and the articles sufficiently tortuous that airborne microbes are inhibited from recontaminating decontaminated articles;

a second inlet for receiving the anti-microbial fluid;

a distribution port assembly removably connected with the second inlet and having at least one fitting for interconnection with an interior passage of at least one of the articles received in the cassette for microbial decontamination;

a cassette top portion matingly receivable on the cassette lower portion in an airborne microbe blocking relationship.

13. The cassette as set forth in claim 12 wherein a plurality of the articles are received in the cassette and further including:

a plurality of interchangeable fluid distribution ports, with different numbers of nipples;

tubing for connecting the nipples with interior passages Of the plurality of the articles received for decontamination.

14. The cassette as set forth in claim 12 wherein the second inlet further includes a check valve which is biased to a closed position to prevent an ingress of microbial contaminants and which check valve is selectively opened under pressure of received anti-microbial fluids.

15. A cassette for receiving articles to be microbially decontaminated, the cassette comprising:

a lower cassette portion;

a first fluid inlet for receiving an anti-microbial fluid to fill the cassette;

a baffle disposed adjacent the first fluid inlet for providing a tortuous path between the first fluid inlet and articles received in the cassette for microbial decontamination, the baffle rendering a path between the first inlet and the articles sufficiently tortuous that airborne microbes are inhibited from recontaminating decontaminated articles;

a second inlet for receiving the anti-microbial fluid;

a distribution port having a plurality of nipples connected with the second inlet;

tubing for selectively interconnecting the nipples with internal passages of the articles received in the cassette for microbial decontamination;

a cassette top portion matingly receivable on the cassette lower portion in an airborne microbe blocking relationship.

\* \* \* \* \*